United States Patent
Thornton et al.

(10) Patent No.: US 6,446,511 B1
(45) Date of Patent: Sep. 10, 2002

(54) METHOD AND SYSTEM FOR TESTING A JOINT WHICH JOINS A FIRST MEMBER WITH A SECOND MEMBER

(75) Inventors: Robert T. Thornton, Clarkston; Pei-Chung Wang, Troy; James Franklin Hengel, Romeo; David P. Kelly, Rochester Hills, all of MI (US)

(73) Assignee: General Motors Corporation, Detroit, MI (US)

( * ) Notice: Subject to any disclaimer, the term of this patent is extended or adjusted under 35 U.S.C. 154(b) by 47 days.

(21) Appl. No.: 09/692,981

(22) Filed: Oct. 23, 2000

(51) Int. Cl.$^7$ ................................................. G01N 3/20
(52) U.S. Cl. ................................................. 73/850
(58) Field of Search .................... 73/826, 830, 831, 73/832, 835, 849, 850, 851, 852

(56) References Cited

U.S. PATENT DOCUMENTS

| | | | | |
|---|---|---|---|---|
| 3,983,745 A | * | 10/1976 | Juusola | 73/91 |
| 4,159,650 A | | 7/1979 | Maguire | 73/847 |
| 5,699,274 A | * | 12/1997 | Starostovic, Jr. | 73/852 |
| 5,764,859 A | | 6/1998 | Kim et al. | 395/22 |
| 6,053,052 A | * | 4/2000 | Starostovic | 73/851 |
| 6,205,862 B1 | * | 3/2001 | Nakamura et al. | 73/796 |

* cited by examiner

*Primary Examiner*—Max Noori
(74) *Attorney, Agent, or Firm*—Jeffrey A. Sedlar; George A. Grove

(57) ABSTRACT

A method and system for testing joints which join one member to another member are disclosed. The method and assembly are capable of non-destructively testing joints which join such members without damaging the members or the joints.

18 Claims, 2 Drawing Sheets

METHOD AND SYSTEM FOR TESTING A JOINT WHICH JOINS A FIRST MEMBER WITH A SECOND MEMBER

TECHNICAL FIELD

The present invention relates to a method and system for the testing of a joint which joins at least two members. More specifically, the present invention relates to a method and system for the non-destructive testing of a joint that joins a fastener or other first member with a second member.

BACKGROUND OF THE INVENTION

In a variety of manufacturing and other applications, fasteners or other members are joined to a member or substrate with joints such as adhesives, welds, or the like. For example, and without limitation, in the automotive vehicle industry, fasteners such as nuts or other fasteners are often welded to portions of a vehicle such that bolts or other fasteners may later be threaded into or otherwise attached to those nuts or other fasteners. In one particular non-limiting example, an automotive vehicle may include a cross member on a floor of the vehicle, wherein the cross member includes nuts that are welded to the cross member such that bolts may be attached or fastened to those nuts to anchor a vehicle seat or other structure to the cross member.

To help assure desired quality, it is preferable that the joint between such a fastener and an associated joint member be tested. Destructive testing techniques are popular, but these require the destruction of either the joints, members or fasteners, thereby rendering the assembly a waste. There is, therefore, a need for a substantially non-destructive method and system for reliably and reproducibly testing joints which join members such as fasteners to other members or substrates.

Even more specifically, in the automotive vehicle industry, there is a need to test the quality of a joint such as a weld or an adhesive joint which joins fasteners such as nuts, bolts, studs or the like to other members of the vehicle. It is particularly desirable to test the quality of production joints regularly during the vehicle assembly process, in an efficient and cost-effective manner.

SUMMARY OF THE INVENTION

According to a first aspect of the present invention, there is provided a method for testing first members which are joined to second members with joints. The method includes collecting reference data relating to strain or displacement of a first joint which attaches a first member to a second member as a first load is exerted upon the first joint, the first joint having a first elastic limit and the first load straining the first joint beyond the first elastic limit, and the first load placing a tensile stress upon the first joint; collecting test data relating to strain of a second joint which attaches a third member to a fourth member as a second load is exerted upon the second joint, the second joint having a second elastic limit, the second load straining the second joint only within the second elastic limit and the second load placing a tensile stress upon the second joint; and comparing the test data to the reference data to determine if the test data is within a predetermined tolerance limit from the reference data.

According to a second aspect of the present invention, there is disclosed a method for testing a fastener which is attached with a joint to a generally planar member having a hole, the fastener attached to the member adjacent and/or covering the hole. The method includes exerting a load upon the joint with a contacting member that can selectively extend through the hole, the load causing a tensile stress upon the joint, and the method includes monitoring the strain or displacement of the joint as the load is exerted.

According to a third aspect of the present invention, there is disclosed a system for testing fasteners which are attached to members. The system includes a punch which is capable of exerting a load upon a joint which attaches a fastener to a member; a load cell operatively connected to the punch, the load cell capable of determining the amount of the load exerted by the punch; a support member for supporting the first member as the load is exerted upon the joint; and a deflection meter which is capable of measuring the amount of deflection experienced by the joint due to the load.

These and other objects, aspects, and advantages of the present invention will become apparent upon reading the following detailed description in combination with the accompanying drawings.

DESCRIPTION OF THE PREFERRED EMBODIMENT

In the most general form, the present invention provides a method and a system or assembly for non-destructively testing joints which join a first member to a second member.

Figure 2:
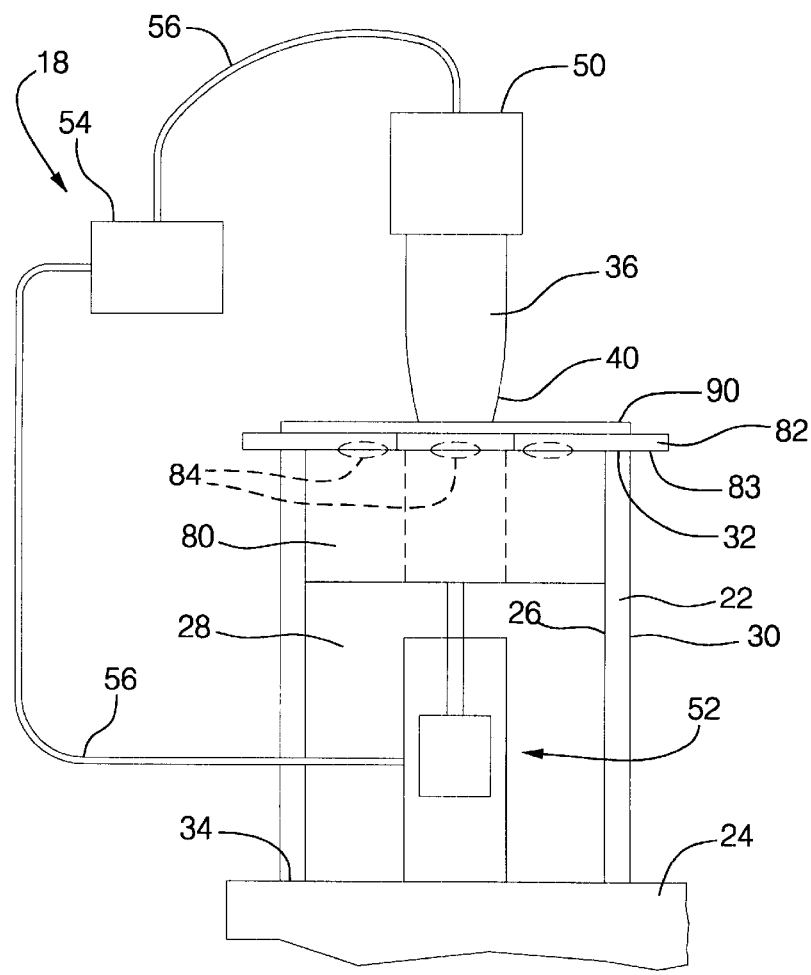
FIG. 2 illustrates a schematic view of a system for testing joints according to a non-limiting aspect of the present invention.
Figure 3:
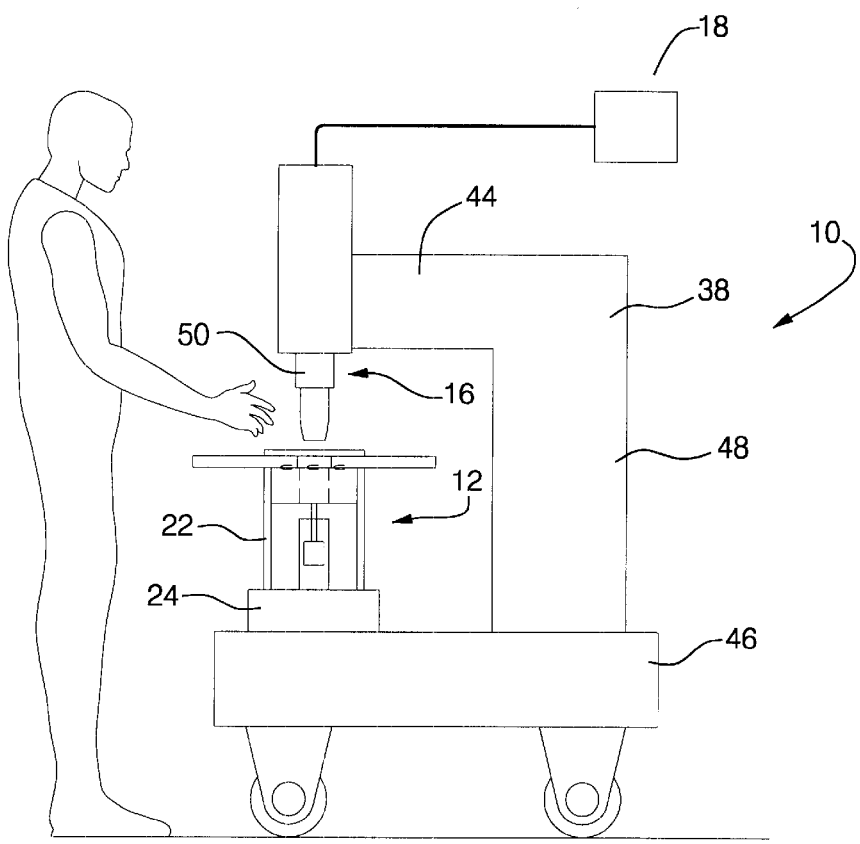
FIG. 3 illustrates a schematic view of a system for testing joints according to a non-limiting aspect of the present invention.

Referring to FIGS. 2 and 3, there is illustrated one embodiment of a testing system or assembly 10 which may be used for non-destructively testing joints which join or attach or assist in joining or attaching a first member such as a fastener to a second member. The system 10 includes a support assembly 12 and a force or stress applicator assembly 16 in communication with a data collector assembly 18.

In the non-limiting embodiment shown, the support assembly 12 includes a support member 22 (e.g., a die) which optionally is supported by a base member or stand 24. The support member 22 has a first surface for receiving a workpiece, which first surface has a recess or aperture defined therein. For instance, in one embodiment, though other shape or configurations may be used, the support member 22 is substantially cylindrical or annular and includes a substantially annular or cylindrical inner surface 26 which substantially defines and at least partially surrounds an internal open cylindrical portion 28. In that embodiment, the support member 22 also includes a substantially annular or cylindrical outer housing 30 and first and second generally horizontal end surfaces 32, 34, the first end surface 32 suitable for receiving or supporting the workpiece. In a non-limiting embodiment, the support member 22 may be integral with or detachably fastened to a holder (not shown). The holder may include a portion (e.g., a flat portion) which supports the support member 22 adjacent to or at the second end surface 34 of the support member 22. For instance, the generally flat portion of the holder may be attached to the support member 22 with one or more screws, bolts or other fastening members. Alternatively, the holder may be integrally formed with the support member 22. The person of skill in the art will recognize that the support member 22 may be formed in a variety of configurations including, but not limited to, having a cross-section which is triangular, rectangular, elliptical, polygonal or some combination of lines and/or curves. Furthermore, there may be more than one support member 22 and the support members 22 may be interchangeable. The support member 22 may also be specifically designed or adapted to receive and support (e.g., in a mating engagement) a specifically configured workpiece having a predetermined configuration or a particular member which is joined to a particular fastener with a joint (e.g., a weld).

The stand 24 is a substantially rectangular or square box or block. However, the stand may be in a variety of other configurations which include, but are not limited to, rectangular, triangular, elliptical, circular, polygonal or other three dimensional configurations. It may be solid, hollow or comprised of a plurality of frame members. In a further non-limiting embodiment, the stand 24 may include one or more recesses or cavities for selectively receiving a fastener, member or portion of the holder or support member. The person of skill in the art will understand that there are several manners in which the support member 22 or the holder may be detachably or relatively permanently attached to the stand 24 within the scope of the present invention. The present illustrated embodiments are not intended as limiting In one embodiment, the support member 22 and the stand 24 are formed at least partially of a metal such as an aluminum, steel or a combination thereof. In alternative embodiments, the stand 24, the support member 22 or the holder may be formed from a variety of other materials such as plastic, composite or other suitable material. The choice of material or materials used may depend on the manner in which the stand 24, the support member 22, or the holder will be utilized. In another alternative embodiment, the support assembly 12 may only include the support member 22. In still another alternative embodiment, the testing system 10 may omit the support assembly 12.

One preferred force applicator assembly 16 includes a contacting member 36 (such as a punch) and an actuator 38 (such as a press, a push-off tester, or a hydraulic assembly) for actuating the contacting member 36. By way of example, the contacting member 36 may be generally elongated with a free end. For instance, a punch 36 may be employed that is generally cylindrical, and terminates at a substantially spherical or elliptical contacting surface 40. In one embodiment, the contacting member 36 is formed of a suitable hardened plastic or metal; however, the contacting member could also be selected from a variety of other suitable materials. The person of skill in the art will recognize that the contacting member 36 may be provided in a variety of cross-sectional geometric configurations including, but not limited to, rectangular, triangular, elliptical, polygonal, or other combinations of lines and curves. In an alternative embodiment, the contacting member 36 may be truncated or blunted. It shall further be recognized that the choice of shape and material used for the contacting member 36 may be a selective choice based upon the manner in which the contacting member 36 will be utilized.

In one particular preferred embodiment, the actuator 38 is a press or push-off tester 38 which may be operated manually or automatically. The press 38 includes upper and lower portions 44, 46 and a central portion 48 attached to the upper and lower portions 44, 46. In the non-limiting embodiment shown, the press 38 includes a conventional hydraulic assembly (not shown) for actuating the contacting member 36. In further non-limiting embodiments, the press may also include a push button (not shown) electrically coupled to the hydraulic assembly or a crank (not shown) mechanically coupled to the hydraulic assembly for actuating the hydraulic assembly. It shall be recognized that the actuator 38 may be provided in a variety of configurations without departing from the scope of the invention. In alternative embodiments, the actuator 38 may thermally, electrically or magnetically actuate the contacting member 36. The actuator 38 may assume any of a variety of configurations for allowing the contacting member 36 to be actuated as needed or desired.

In a particularly preferred embodiment, the data collector assembly 16 includes a stress or force meter 50, a strain or displacement meter 52 and a data storage unit 54. The force meter 50 and the displacement meter 52 may be operatively and communicatively coupled to the data storage unit 54 via conventional busses or wires 56 or by some other method which may include direct or remote communication. In the particular embodiment shown, the displacement meter 52 is an extensometer or linear variable displacement transducer 52, the force meter 50 is a conventional load cell 50 and the data storage unit 54 is associated with the memory of a suitable computer 54 (e.g., a personal computer). The load cell may be chosen from a myriad of commercially available load cells or may be specially designed. It shall be recognized that other data collection systems may be used according to the present invention. Moreover, the data collection system may output information or data to a suitable read out device such as a computer video monitor, a printer or the like. Data or information may also be written to a suitable storage media (e.g., diskette, CD, DVD or the like for long term storage of data).

Assembly

Without intending to be limited thereby, in one embodiment of the testing assembly 10, the support assembly 12 is placed operatively adjacent the stress applicator assembly 16. For instance, in the embodiment shown, the stand 24 of the support assembly 12 is placed upon the lower portion 46 of the press 38. The cylindrical support member 22 is placed upon the stand 24 but below the punch 36 such that the inner open portion 28 of the support member 22 is open for receiving the punch 36 to enable the punch 36 to be selectively actuated into and out of or toward and away from at least a portion of the inner open portion 28 of the support member 22. The stand 24 may be suitably attached (e.g., welded, screwably or otherwise fastened) to or integrally formed with the actuator or press 38. In further non-limiting embodiments, the support member 22 may be attached to the stand 24 or the actuator 38 or some other support. Preferably, the support member 22 is interchangeable with other support members 22 and is therefore releasably fastened to the stand 24 or holder. In non-limiting embodiments, the system 10 includes a plurality of support members 22 each having an end specifically designed to be selectively placed in the holder that is attached to the stand 24 or a plurality of holder/support member combinations which may be selectively attached to the stand 24, the press 38, or otherwise supported. In alternative embodiments, the support member 22 or the holder of the support member 22 may be threadably fastened to the stand 24 with a bolt or otherwise fastened to the stand 24. In one embodiment, the holder or support member 22 may include a member that is specially adapted to detachably or releasably fasten to the cavity or aperture (not shown) in the stand 24. In still other alternative embodiments, the support member 22 may be integrally formed with or detachably fastened to a portion of the press 38 or other actuator 38 or supporting member or the floor.

To further assemble the testing system 10, the data collector assembly 18 is physically or at least communicatively (e.g., in signaling communication) coupled to the force applicator assembly 16. For instance, the force meter 50 may be coupled to the force applicator assembly 16 for monitoring a response to application of a load by the stress applicator assembly 16. In the embodiment shown, the load cell 50 is coupled to the punch 36 and the press 38 for ascertaining the amount of load or force applied by the press 38, the punch 36 or both. In the non-limiting embodiment shown, the load cell 50 is sandwiched between the punch 36 and a portion of the press 38 (e.g., the hydraulic assembly). The load cell 50 may be attached to the hydraulic assembly of the press 38 and to the punch 36 with suitable fasteners such as screws, or other fasteners such that the hydraulic assembly can selectively actuate the punch 36. In an alternative embodiment, the load cell 50 could be integrally formed with the punch 36, the actuator 38 or both.

In a further non-limiting embodiment, the displacement meter 52 is a deflection meter 52 that is operatively adjacent the support assembly 12. In the particular embodiment shown, the deflection meter 52 is an extensometer 52, which is located within and is substantially surrounded by the support member 26. The deflection meter 52 may be attached to the support member 22, the holder upon which the support member resides, the stand 24, the press 38 or otherwise depending upon the configuration of the testing system 10.

Figure 1:
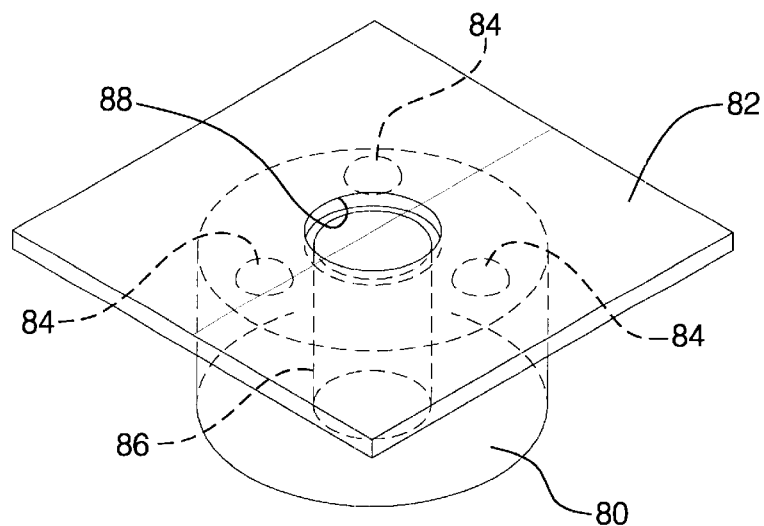
FIG. 1 illustrates a perspective view of a fastener joined with a member according to a non-limiting aspect of the present invention.

In one particular embodiment, and referring to FIGS. 1, 2 and 3, there is shown a fastener 80 such as a nut 80 attached to a sheet metal planar member 82 preferably by one or a plurality of welds 84 (e.g., resulting from projections welding or otherwise). In the embodiment shown, the nut 80 is attached to a planar surface 83 of the planar member 82.

The nut 80 has an aperture 86 extending through it, and the planar member 82 has an aperture 88 extending through it. Preferably, the nut 80 is attached to the planar member 82 such that their respective apertures 86, 88 are generally in registered alignment with each other.

The planar member 82 is placed upon the support member 22 so that the nut 80 extends into the open portion 28 of the support member 22 and the upper annular surface 32 of the support member 22 abuttingly contacts the planar surface 83 of the planar member 82. Preferably, a portion, of the inner surface 26 of the support member 22 is near (e.g., less than 10 centimeters away from, but more preferably within 1 centimeter and even more preferably within 1 millimeter) and substantially surrounds the nut 80 Preferably the upper surface 32 of the support member 22 contacts the planar surface 83 of the planar member 82 less than 10 centimeters away from, but more preferably within about 1 centimeter and even more preferably within 1 millimeter of the nut 80 or welds 84. Once the planar member 82 and nut 80 are positioned upon the support member 22, a binder 90 may be positioned upon the member 82 to hold the member 82 in place. In a non-limiting embodiment, the binder 90 is a ring-type clamp or grip that can be screwably or otherwise detachably fastened to the die or support member 22. It shall be recognized, however, that clamps or other members other than ring clamps may be used to help secure a member in place.

Once the first and second members are positioned upon the support member 22, the force applicator assembly 16 applies a load upon the joint 84. The data collection assembly 18, in turn, gathers and stores retrieval data regarding the load applied to the joint 84 and the response (e.g., deflection, displacement, or other deformation, whether plastic or elastic) of the joint 84.

Thus, the press 38 lowers the punch 36 through the aperture 88 of the planar member 82 and into contact with the nut 80. Thereafter, the press 38, the punch 36 or both exert a load upon the nut 80 which, in turn, places a load upon the welds 84. In the embodiment shown, the load exerted generally creates tension in the welds 84. In alternative embodiments, a shear, compressive or other stress may be induced. The person of skill in the art will recognize that a variety of arrangements, similar to the member 82 and fastener 80 shown, have fasteners welded to members over holes in such members such that the fasteners can be contacted through such holes in the members. The person of skill in the art will further recognize that such arrangements are particularly amendable to testing with the methods and systems of the present invention.

As the load is exerted, the load cell 50 measures and transmits data to the data storage unit (e.g., the computer) 54 about the load exerted by the force applicator assembly 16. Furthermore, the extensometer 52 measures and transmits values to the computer 54 for the distance which the nut 80 is deflected or displaced away from the planar member 82. The information, in turn, is translatable to stress and strain values for the given load.

It will be recognized that the load may be applied manually, such as by turning the crank of the press 38. In another non-limiting embodiment, the push button is depressed and an electrical signal is sent to the hydraulic assembly of the press 38 to automatically actuate the punch 36. The load applied to the weld may be variable, continuously increasing, intermittently, monotomically or stepwise increasing, decreasing or the like.

The person of skill in the art will recognize that systems such as the system 10 and the like may be suitable in a variety of manufacturing environments. For example, the system 10 may be placed at or near an assembly line for automotive vehicles to test joints of components of automotive vehicles.

As gleaned elsewhere herein, according to one step of the method of the present invention, reference data is collected about one or more reference joints that join a first member to a second member. For example, reference data is collected about the stress/strain relationship (through failure,) of a particular weldment, which is then stored for comparison with later tests.

More specifically, the testing assembly 10 shown in FIGS. 1, 2, and 3 is used to place a load upon one or more reference joints so that reference data may be collected about such joints. The reference data is collected by the data collector assembly 18 as the force applicator assembly 16 places or applies an increasing load upon the joint 84. In particular, as the load is applied, the stress meter 50 continuously measures and transmits amounts or values for the load applied to the joint 84 and the displacement meter 52 continuously measures and transmits amounts or values for the displacement or deflection experienced by the fastener 80, member 82 and/or the joint 84. In situations where the system 10 of the present invention is used for testing a plurality of substantially similar weldments, for example, weldments prepared in a production line using the same production process, for purposes of establishing reference data, at least one reference weldment, preferably is tested to failure. The resulting data can be stored. Thereafter, weldments need only be tested in the elastic deformation region for assuring quality, consistency or both. Thus, loads are applied to further weldments. The deflection is measured and compared with the deflection observed in the reference sample or samples. If there is a substantial variance of the deflection of the given stress, the tested weldment is flagged for further investigation or otherwise removed from production.

In the step of collecting reference data, the load is applied increasingly through the elastic deformation region, plastic deformation or even failure. In an alternative embodiment, the load continues to increase until the joint nearly reaches its elastic limit. In still another alternative embodiment, the load continues to increase until the joint surpasses its elastic limit.

Figure 4:
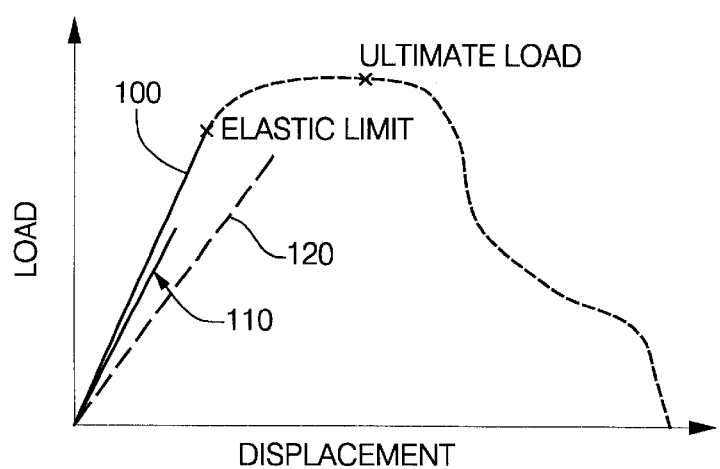
FIG. 4 illustrates a graphical representation of data collected according to a non-limiting aspect of the present invention.

As the data collector assembly collects reference data, a visual depiction of the data may be displayed, such as by a video monitor, a printout or the like. For instance, the computer 54 may plot a graph of the load-displacement relationship observed. An exemplary graph is illustrated in FIG. 4 pursuant to which a load is applied to a weldment until plastic yield is observed in the weldment. As shown, the graph includes a reference curve 100 which represents the load applied to the fastener versus the displacement of the weld.

In alternative embodiments, the reference data may be data which is collected by using engineering judgment and/or known information to determine a required or desired strength for a joint. In such embodiments, tests may be performed or reference data may be collected without actually testing specific reference joints. Rather, and for example, data may be available or collectable regarding how much force a joint can desirably withstand and that data may be used as reference data.

In an exemplary embodiment of the invention, the testing assembly 10 shown in FIGS. 1, 2, and 3, is used to place a load upon one or more production weldments. In one particular embodiment, the assembly is used to test production weldments at or near an automotive vehicle assembly line. Test data is collected by the data collector assembly 18 as the force applicator assembly 16 applies an increasing load upon the weldment 84. As the load is applied, the force meter 50 continuously measures stress or load applied and the displacement meter 52 measures the deflection or displacement experienced by the fastener 80, member 82 and/or the joint or weldment 84. Inasmuch as the test part is a production weldment, for which non-destructive methods are desired, the load is applied to an amount below the load amount required in the reference for plastic yield of the weldment 84. Data is obtained much like for the reference weldment.

According to another step of the invention, the reference data collected is compared with the test data collected from one or more production weldments to ascertain whether they correspond or fall within a predetermined tolerance range.

In one embodiment of the invention, the computer includes a program for comparing the test data and the reference data. For example, the computer may be preprogrammed with a deviation point or curve which represents the predetermined deviation away from the reference data which the test data is desirably or required to be within. For example, and referring to FIG. 4, there is shown a deviation curve 120. In the embodiment shown, the curve 120 represents the maximum amount or amounts of displacement of the test joint allowed for various loads that may be placed upon the weld which attaches a first member to a second member. If test data for a given joint which attaches a first member to a second member falls or extends to the right of the deviation curve 120, then the joint is inadequate to secure a fastener to the planar member and the weld is rejected. If the test data is to the left of the curve, the weld is adequate and may be used in an article of manufacture.

In another embodiment, the computer calculates the slope of the reference curve 100 and the slope of the test curve 110 and compares the two slopes to help assure that the slope of the test curve 110 is within a predetermined tolerance limit from the slope of the reference curve 100. In still another embodiment, a test weld may be tested to a predetermined load to determine if the displacement or test data of the test joint is within a predetermined tolerance limit from the reference data at the predetermined load.

The person of skill in the art will recognize that a variety of other characteristics or properties may be tested within the scope of the present invention to compare test data to reference data.

It shall further be recognized that comparing reference data to test data allows test data to be collected upon one or many different test joints without destroying the joints or the members which are joined by the test joints. According to the present invention, an assembly such as the testing assembly 10 of the present invention is employed in a manufacturing environment such as an automotive vehicle assembly line and the welds are tested before, after or during the assembly of the members in articles of manufacture such as automotive vehicles. All welds in the line may be tested, random welds may be tested, or testing may be done according to a predetermined sequences.

According to yet another step of the invention, a signal may be selectively formed based upon the comparing of test data and reference data. In one embodiment, a signal is formed or created when the test data is beyond the predetermined deviation away or tolerance limit from the reference data. According to a non-limiting embodiment, the computer 54 can be programmed to generate an alarm when the test data measured is outside of the predetermined deviation from the reference data. In one embodiment, the computer may show where the test data is outside of the predetermined deviation or tolerance limit. In alternative embodiments, there may be a visual or audible signal, such as the word "reject" or some other visual icon displayed by the computer or a beep or other sound emitted by the computer. Furthermore, other signals may be produced by other memory units. The person of skill in the art will recognize that a variety of signals may be produced within the scope of the present invention.

It should be understood that the invention is not limited to the exact embodiment or construction which has been illustrated and described but that various changes may be made without departing from the spirit and the scope of the invention.

What is claimed is:

1. A method for testing first members which are joined to second members with joints, said method comprising the steps of:

collecting reference data relating to displacement of a first joint which attaches a first member to a second member as a first load is exerted upon said first joint, said first joint having a first elastic limit and said first load straining said first joint beyond said first elastic limit, and said first load placing a tensile stress upon said first joint;

collecting test data of an automotive vehicle assembly line relating to displacement of a second joint which attaches a third member to a fourth member as a second load is exerted upon said second joint, said second joint having a second elastic limit, said second load straining said second joint only within said second elastic limit and said second load placing a tensile stress upon said second joint; and comparing said test data to said reference data to determine if said test data is within a predetermined tolerance limit from said reference data.

2. A method as in claim 1 further comprising, selectively forming a signal based upon said step of comparing the displacement of the first joint to the displacement of the second joint.

3. A method as in claim 2, wherein said step of selectively forming said signal includes forming said signal when the test data is a predetermined amount different than the reference data.

4. A method as in claim 1, further comprising utilizing said second member within an article of manufacture.

5. A method as in claim 1, wherein said first member and said third member are fasteners and said second member and said fourth member include holes through which a contacting member is extended to apply said first load and said second load.

6. A method as in claim 5, wherein said first load is applied with a first punch that is specially adapted to contact said fasteners.

7. A method as in claim 1, wherein said first load is substantially identical to said second load.

8. A method for testing a weld, said method comprising the steps of:

providing a fastener attached with said weld to a generally planar member, said generally planar member having a hole, said fastener attached to said member adjacent said hole, said member being a component of an automotive vehicle;

exerting a load upon said weld of an automotive vehicle assembly line with a contacting member by extending said contacting member through said hole, said load causing a tensile stress upon said weld; and monitoring the displacement of the weld as said load is exerted.

9. A method as in claim 8 wherein said contacting member is a punch designed to contact said fastener after said punch extends through said hole.

10. A method as in claim 9 wherein said fastener is selected from a nut or a bolt or a stud.

11. A method as in claim 8 further comprising placing said planar member upon a support member prior to said step of exerting said load, said support member including a cavity for receiving said fastener when said member is placed upon said support member.

12. A system for testing welds comprising:

a punch which is adapted for extending through a hole in a member to contact a fastener thereby exerting a load upon a weld which attaches said fastener to said member, said member being a component of an automotive vehicle;

a load cell operatively connected to said punch, said load cell capable of determining the amount of said load exerted by said punch;

a support member for supporting said first member as said load is exerted upon said weld; and a displacement meter which is capable of measuring the amount of displacement experienced by said weld due to said load.

13. A system as in claim 12 wherein said displacement meter is an extensometer.

14. A system as in claim 12 further comprising a data acquisition device which is communicatively coupled to the load cell and the displacement meter.

15. A system as in claim 14 wherein data acquisition device is a computer which is capable of comparing data.

16. A system as in claim 14 wherein said data acquisition is capable of receiving and storing data and is capable of triggering a signal based upon said data.

17. A system as in claim 12 wherein said fastener is a nut.

18. A system as in claim 12 wherein said support at least partially supports said member at an area that is within one millimeter of the said fastener.

* * * * *